US 11,486,831 B2

(12) United States Patent
Tono et al.

(10) Patent No.: US 11,486,831 B2
(45) Date of Patent: Nov. 1, 2022

(54) SPECIMEN MEASUREMENT DEVICE AND CONTROL METHOD OF SPECIMEN MEASUREMENT DEVICE

(71) Applicant: CANON MEDICAL SYSTEMS CORPORATION, Otawara (JP)

(72) Inventors: Ichiro Tono, Otawara (JP); Takeshi Yamauchi, Utsunomiya (JP); Shoichi Kanayama, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/940,570

(22) Filed: Jul. 28, 2020

(65) Prior Publication Data

US 2021/0033539 A1 Feb. 4, 2021

(30) Foreign Application Priority Data

Aug. 1, 2019 (JP) .............................. JP2019-142423

(51) Int. Cl.
*G01N 21/77* (2006.01)
*G01N 21/17* (2006.01)
(Continued)

(52) U.S. Cl.
CPC ....... *G01N 21/7703* (2013.01); *G01N 21/552* (2013.01); *G01N 33/54333* (2013.01);
(Continued)

(58) Field of Classification Search
CPC ............. G01N 21/7703; G01N 21/552; G01N 2021/1727; G01N 2021/7716; G01N 2021/7736
See application file for complete search history.

(56) References Cited

U.S. PATENT DOCUMENTS 7,512,298 B2   3/2009   Yi et al.
7,702,202 B2   4/2010   Koch et al.
(Continued)

FOREIGN PATENT DOCUMENTS

JP   2010-511872 A   4/2010
JP      5814806 B2   11/2015
(Continued)

*Primary Examiner* — Samuel P Siefke
*Assistant Examiner* — Henry H Nguyen
(74) *Attorney, Agent, or Firm* — Oblon, McClelland, Maier & Neustadt, L.L.P.

(57) ABSTRACT

A specimen measurement device which detects a measurement object material according to the present embodiment, includes: a magnetic field applicator configured to apply a magnetic field to a measurement cartridge including a substrate, a first substance fixed on the substrate and specifically reacting with the measurement object material, a magnetic particle, and a substance fixed on the magnetic particle and specifically acting with the measurement object material; a detector configured to detect light passing through the substrate; and a controller configured to control the magnetic field applicator to perform a first operation to apply a first magnetic field in a direction to move the magnetic particle away from the substrate when a specimen solution containing the measurement object material is introduced into the measurement cartridge, and then perform a second operation to apply a second magnetic field in a direction to move the magnetic particle toward the substrate.

13 Claims, 7 Drawing Sheets

(51) Int. Cl.
*G01N 21/552* (2014.01)
*G01N 33/543* (2006.01)

(52) U.S. Cl.
CPC ............... *G01N 2021/1727* (2013.01); *G01N 2021/7716* (2013.01); *G01N 2021/7736* (2013.01); *G01N 2446/00* (2013.01)

(56) References Cited

U.S. PATENT DOCUMENTS

| | | | |
|---|---|---|---|
| 7,903,240 B2 | 3/2011 | Smith et al. | |
| 9,274,104 B2 | 3/2016 | Tono et al. | |
| 9,841,419 B2* | 12/2017 | Kelly | G01N 33/54366 |
| 10,317,256 B2 | 6/2019 | Raghavan et al. | |
| 10,317,399 B2 | 6/2019 | Ikeda et al. | |
| 2008/0101991 A1* | 5/2008 | Nakamura | B01F 13/0059 |
| | | | 422/68.1 |
| 2008/0129997 A1 | 6/2008 | Yi et al. | |
| 2008/0131049 A1 | 6/2008 | Koch et al. | |
| 2008/0291446 A1 | 11/2008 | Smith et al. | |
| 2010/0188076 A1* | 7/2010 | Kahlman | G01R 33/1269 |
| | | | 324/232 |
| 2010/0324828 A1 | 12/2010 | Kahlman et al. | |
| 2012/0252111 A1 | 10/2012 | Tono et al. | |
| 2014/0205996 A1* | 7/2014 | Lizzi | B03C 1/286 |
| | | | 435/5 |
| 2015/0177125 A1* | 6/2015 | Kasai | G01N 33/54333 |
| | | | 422/69 |
| 2017/0108495 A1 | 4/2017 | Ikeda et al. | |
| 2018/0299301 A1 | 10/2018 | Raghavan et al. | |

FOREIGN PATENT DOCUMENTS

| | | |
|---|---|---|
| JP | 2017-75938 A | 4/2017 |
| JP | 2018-177527 A | 11/2018 |
| WO | WO 2010/044005 A2 | 4/2010 |
| WO | WO 2010/044007 A2 | 4/2010 |

* cited by examiner

SPECIMEN MEASUREMENT DEVICE AND CONTROL METHOD OF SPECIMEN MEASUREMENT DEVICE

CROSS REFERENCE TO RELATED APPLICATIONS

This application is based upon and claims the benefit of priority from the prior Japanese Patent Application No. 2019-142423, filed on Aug. 1, 2019, the entire contents of which are incorporated herein by reference.

FIELD

Embodiments described herein relate generally to a specimen measurement device and a control method of the specimen measurement device.

BACKGROUND

A sensitive specimen measurement device for optically measuring an object material in a specimen solution is well known. The specimen measurement device has a sensing area on a surface of an optical waveguide to specifically detect or measure the object material. Such a specimen measurement device includes an optical waveguide having a sensing area in which a first substance that is specifically bonded with the object material is fixed, magnetic particles to which a second substance is fixed, a magnetic field application unit that generates and applies a magnetic field, a light source, and a detection unit that detects light. In the specimen measurement device having such a configuration, the magnetic particles are dispersed over the sensing area, for example via a blocking layer containing a water-soluble material.

In such a conventional specimen measurement device, after a specimen solution is introduced into the reaction space, the blocking layer dissolves and the magnetic particles disperse into the specimen solution. Since the magnetic particles have a relatively large specific gravity, however, they tend to stay near the sensing area. This causes a problem in that it is difficult to improve the reaction efficiency of the object material and the magnetic particles in the specimen solution.

DETAILED DESCRIPTION

Figure 1:
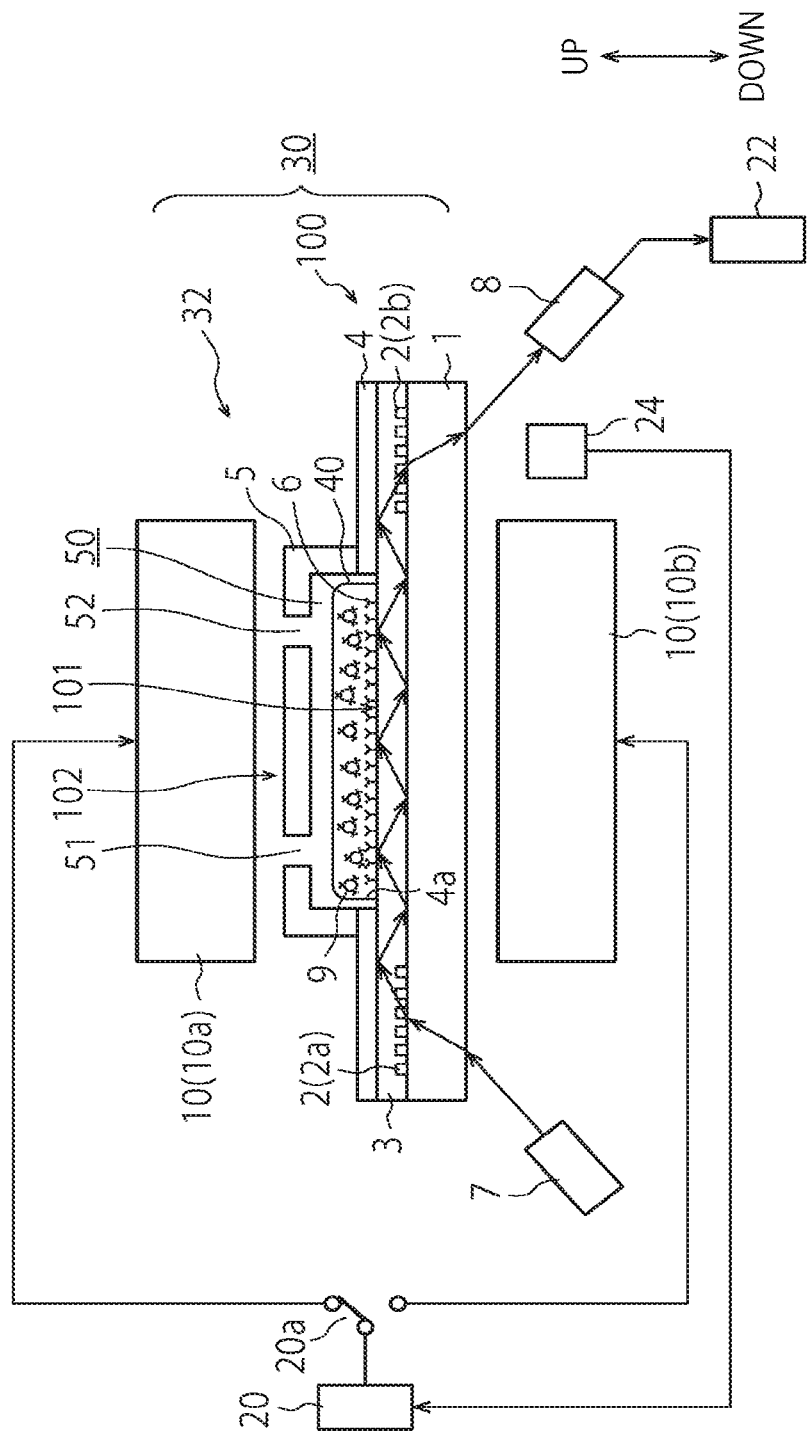
FIG. 1 is a block diagram for explaining an example of the entire configuration of a specimen measurement system according to a first embodiment.

Specimen measurement devices and control methods of the specimen measurement devices according to embodiments will now be described below with reference to the accompanying drawings. In the descriptions below, the same reference numeral is provided to elements having substantially the same function and structure, and a repeated explanation of such elements is provided only when it is needed.

First Embodiment

FIG. 1 is a diagram for illustrating an example of the entire configuration of a specimen measurement system 30 according to a first embodiment. The specimen measurement system 30 shown in FIG. 1 includes a specimen measurement device 32 and a measurement cartridge 100. When the user inserts and sets the measurement cartridge 100 in the specimen measurement device 32, the specimen measurement system 30 according to this embodiment is constituted.

Specifically, the specimen measurement device 32 according to the first embodiment includes a light source 7, a detection unit 8, a magnetic field application unit 10, a control unit 20, a calculation unit 22, and a cartridge sensor 24. The measurement cartridge 100 according to the first embodiment includes a substrate 1, a grating 2, an optical waveguide 3, a protective film 4, a frame 5, and a sealing film 40.

At least one first substance 6 that specifically reacts with a measurement object material 14 (see FIG. 4 through FIG. 6) is fixed to a surface of the optical waveguide 3 in the measurement cartridge 100. The surface of the optical waveguide 3 on which the first substance 6 is fixed forms a sensing area 101. If the measurement object material 14 in a specimen solution is an antigen, for example, the first substance 6 may be an antibody (primary antibody).

The substrate 1 may be, for example, formed of alkali-free glass. The optical waveguide 3 may be, for example a planar optical waveguide. The optical waveguide 3 may be formed of a thermosetting resin such as a phenol resin, an epoxy resin, or an acrylate resin, or a light curing resin. The material used here preferably has a light-transmitting property with respect to some kinds of light, such as a resin having a higher refractive index than the substrate 1. The fixing of the first substance 6 that specifically reacts with the measurement object material 14 in the specimen solution to the sensing area 101, which is a detection face, may be performed by hydrophobic interaction or chemical bonding with the sensing area 101 on the surface of the optical waveguide 3.

The sealing film 40 sealing at least one magnetic particle 9 as well as the first substance 6 is provided on the surface of the optical waveguide 3. At least one second substance 13 that specifically reacts with the measurement object material 14 is fixed on the surface of each magnetic particle 9.

More specifically, the magnetic particle 9 together with the first substance 6 are sealed by the sealing film 40 in the sensing area 101 on the surface of the optical waveguide 3. The sealing film 40 at least contains a water-soluble material. If the specimen solution is introduced in a reaction space 50 within the frame 5, the water-soluble material of the sealing film 40 rapidly dissolves and the magnetic particle 9 disperse into the specimen solution. The frame 5 has an inlet 51 for introducing the specimen solution into the reaction space 50 and an air outlet 52 for evacuating air from the reaction space 50.

In an example of the specimen measurement device 32 shown in FIG. 1, a plurality of the first substances 6 and a plurality of the magnetic particles 9 are provided in the specimen measurement device 32.

Figure 2A:
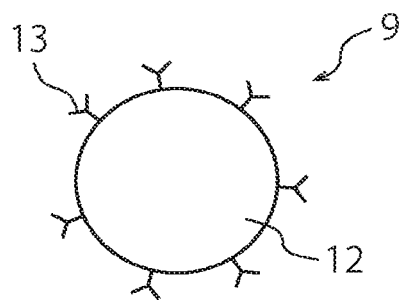
FIG. 2A is a schematic diagram illustrating an example of an external appearance of a magnetic particle.
Figure 2B:
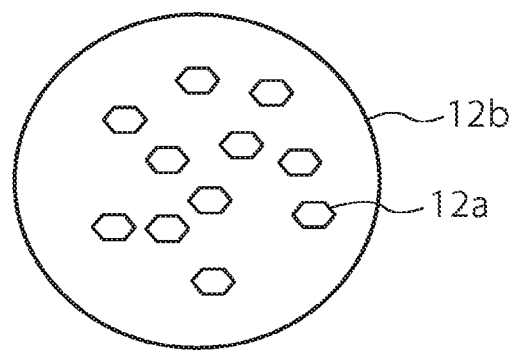
FIG. 2B is a schematic diagram illustrating an example of a cross section of a magnetic particle.
Figure 2C:
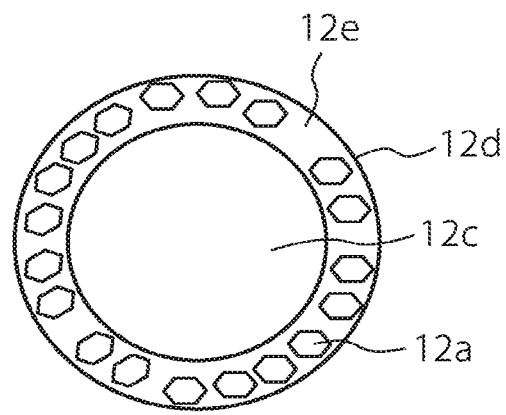
FIG. 2C is a schematic diagram illustrating an example of a cross section of a magnetic particle.

FIGS. 2A to 2C are schematic diagrams illustrating the appearances of the magnetic particle 9. Specifically, FIG. 2A is a schematic diagram illustrating an external appearance of the magnetic particle 9, and FIGS. 2B and 2C are schematic diagrams illustrating cross sections of the magnetic particles 9.

As shown in FIG. 2A, the magnetic particle 9 is formed by fixing at least one second substance 13 on the surface of a fine particle 12. If the measurement object material 14 in the specimen solution is an antigen, for example, the second substance 13 may be an antibody (secondary antibody). In this case, the fine particle 12 may be a fine particle 12b obtained by surrounding magnetic nano fine particles 12a with a high molecular material as shown in FIG. 2B, or a fine particle 12d including a core 12c and a shell 12e disposed to surround the core 12c as shown in FIG. 2C. The shell 12e may be formed of a high molecular material and include the magnetic nano fine particles 12a.

The combination of the measurement object material 14, the first substance 6, and the second substance 13 is not limited to the combination of an antigen and antibodies as described above. For example, a combination of a sugar and a lectin, a combination of a nucleoside chain and a complementary nucleoside chain, or a combination of a ligand and a receptor may also be used.

Referring again to FIG. 1, an incoming side grating 2a and an outgoing side grating 2b are disposed at both ends of the surface of the substrate 1 or at both ends of the optical waveguide 3. The substrate 1 is formed of, for example, alkali-free glass. The optical waveguide 3 is disposed on the surface of the substrate 1.

The protective film 4 is coated on the optical waveguide 3. For example, the protective film 4 is a resin film having a low refractive index. The protective film 4 has an opening 4a in which a part of the surface of the optical waveguide 3 is exposed between the incoming side grating 2a and the outgoing side grating 2b. The shape of the opening 4a is rectangular for example, when viewed from above. The surface of the optical waveguide 3 exposed in the opening 4a defines the sensing area 101. The frame 5 is disposed on the protective film 4 so as to surround the sensing area 101.

The light source 7 included in the specimen measurement device 32 emits light to the measurement cartridge 100. The light source 7 is a red laser diode, for example. The light emitted from the light source 7 is diffracted by the incoming side grating 2a and propagates through the optical waveguide 3. The light is then diffracted by the outgoing side grating 2b and goes out. The light from the outgoing side grating 2b is received by the detection unit 8 where the intensity of the light is measured. The detection unit 8 is a photodiode, for example.

The magnetic field application unit 10 applies a magnetic field to the measurement cartridge 100. In this embodiment, the magnetic field application unit 10 includes a first magnetic field application unit 10a disposed above the optical waveguide 3 and a second magnetic field application unit 10b disposed below the optical waveguide 3. Each of the first magnetic field application unit 10a and the second magnetic field application unit 10b generates a magnetic field and applies the generated magnetic field to the measurement cartridge 100 to move the magnetic particles 9 in response to the generated magnetic field.

Specifically, the first magnetic field application unit 10a generates an upward magnetic field, which is a magnetic field to move the magnetic particles 9 away from the substrate 1 and the optical waveguide 3, and the second magnetic field application unit 10b generates a downward magnetic field, which is a magnetic field to move the magnetic particles 9 toward the substrate 1 and the optical waveguide 3. Therefore, the direction of the first magnetic field application unit 10a with respect to the substrate 1 and the optical waveguide 3 is set to move the magnetic particles 9 away from the substrate 1 and the optical waveguide 3, and the direction of the second magnetic field application unit 10b with respect to the substrate 1 and the optical waveguide 3 is set to move the magnetic particles 9 toward the substrate 1 and the optical waveguide 3.

Each of the first magnetic field application unit 10a and the second magnetic field application unit 10b includes a magnet or an electromagnet, for example. Although it is preferable that the intensity of the magnetic field be dynamically adjusted by adjusting the current flowing through an electromagnet, the intensity of the magnetic field may be adjusted by adjusting the magnetic intensity of the magnet itself or by adjusting the distance from the measurement cartridge 100, by using a ferrite magnet or the like.

In this embodiment, the magnetic particles 9 adhering to the sensing area 101 not by the antigen-antibody reaction may be removed from the sensing area 101 by a magnetic field applied to the magnetic particles 9 by means of the first magnetic field application unit 10a. This leads to a more accurate measurement of the absorbance due to the magnetic particles 9 bonded to the sensing area 101 via the measurement object material 14 through the antigen-antibody reaction. The application of a magnetic field to the magnetic particles 9 by the second magnetic field application unit 10b causes the magnetic particles 9 to move toward the sensing area 101. Since the magnetic particles 9 may be bonded to the sensing area 101 more easily in this manner, the sensitivity in the detection of the measurement object material 14 may be improved, and the time required for the magnetic particles 9 to precipitate may be shortened.

The fine particles 12 of the magnetic particles 9 preferably have a superparamagnetic property and lose the magnetization immediately after the application of the magnetic field is stopped. As a result, if the magnetic particles 9 agglutinate due to the magnetization caused by the application of the magnetic field, the magnetic particles 9 may be dispersed again by stopping the application of the magnetic field.

In order to perform such a control operation, the control unit 20 included in the specimen measurement device 32 according to the first embodiment controls the first magnetic field application unit 10a and the second magnetic field application unit 10b. Specifically, the control unit 20 controls the timing at which a magnetic field is generated by each of the first magnetic field application unit 10a and the second magnetic field application unit 10b. For example, a switch 20a shared by the first magnetic field application unit 10a and the second magnetic field application unit 10b is provided to the magnetic field application unit 10 to control which of the first magnetic field application unit 10a and the second magnetic field application unit 10b is activated. The control unit 20 also controls the intensity of the magnetic field generated by the first magnetic field application unit 10a or the second magnetic field application unit 10b.

The calculation unit 22 obtains the amount and/or the concentration of the measurement object material 14 by calculation based on the intensity of light outputted from the detection unit 8. The control unit 20 controls the timing at which the calculation unit 22 obtains the intensity of light and performs the calculation.

The cartridge sensor 24 is a detection mechanism provided to detect whether the measurement cartridge 100 is set to the specimen measurement device 32. For example, the cartridge sensor 24 includes a photosensor located below the position where the measurement cartridge 100 is set. The cartridge sensor 24 including the photosensor emits light and detects the presence or the absence of reflected light. The result of the light detection is inputted to the control unit 20. The sensor used for the cartridge sensor 24 is not limited to a photosensor but may be various kinds of sensors. For example, the cartridge sensor 24 may be a contact type sensor, and the setting of the measurement cartridge 100 to the specimen measurement device 32 may be detected by the mechanical contact of the measurement cartridge 100 to the contact type sensor.

The control unit 20 determines whether the measurement cartridge 100 is set based on the detection result of whether the reflected light is detected. If the cartridge sensor 24 detects the reflected light, the measurement cartridge 100 is determined to be set, and if the cartridge sensor 24 does not detect the reflected light, the measurement cartridge 100 is determined not to be set.

Figure 3:
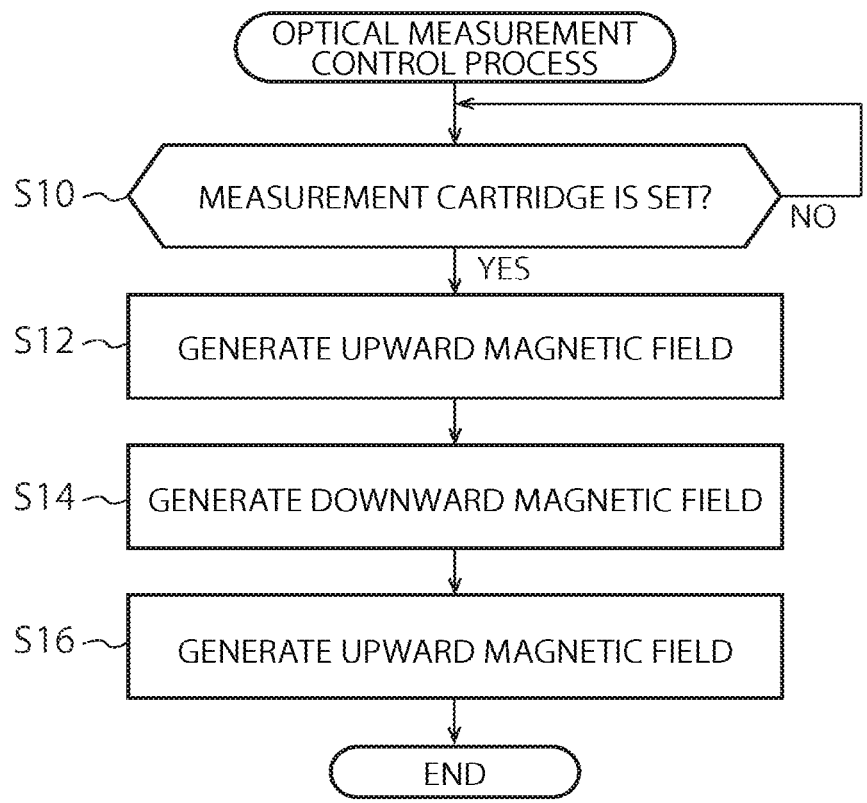
FIG. 3 is a flowchart for explaining the contents of an optical measurement control process performed by the specimen measurement system according to the first embodiment.
Figure 4:
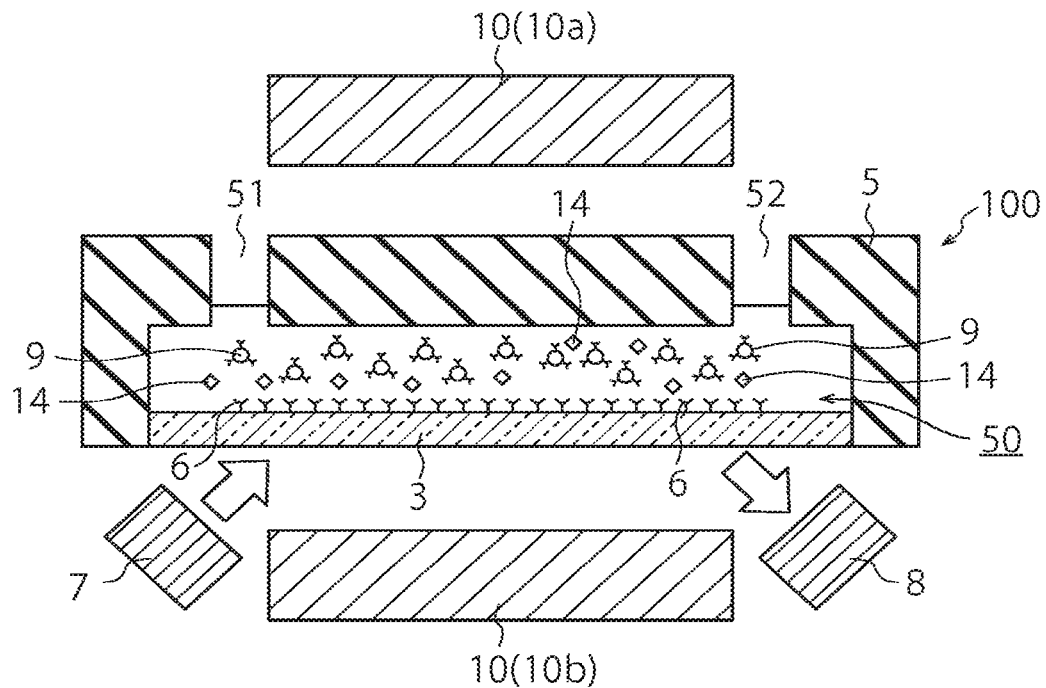
FIG. 4 is a diagram for explaining the state of a specimen solution in a reaction space in step S12 of the optical measurement control process according to the first embodiment.
Figure 5:
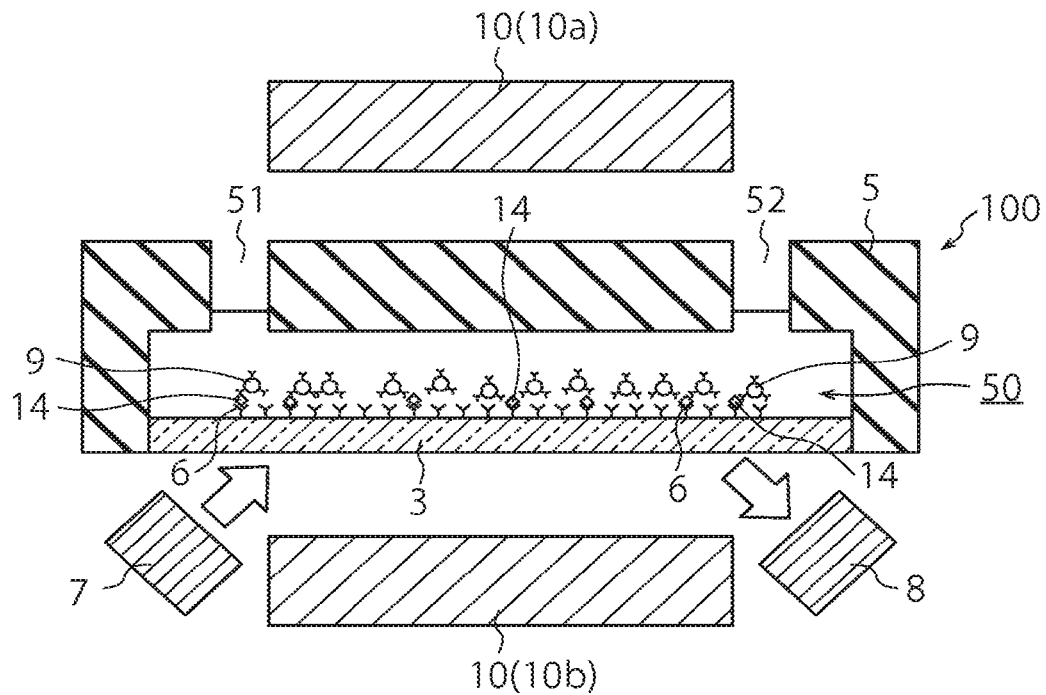
FIG. 5 is a diagram for explaining the state of the specimen solution in the reaction space in step S14 of the optical measurement control process according to the first embodiment.
Figure 6:
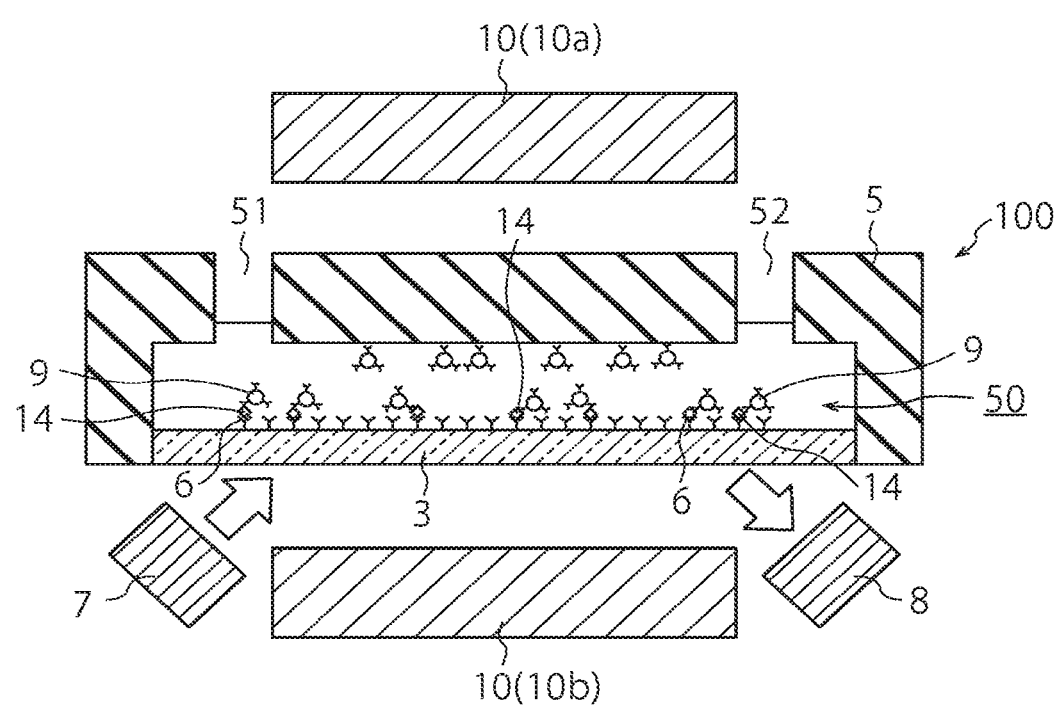
FIG. 6 is a diagram for explaining the state of the specimen solution in the reaction space in step S16 of the optical measurement control process according to the first embodiment.

Next, an optical measurement method of the specimen measurement system 30 according to the first embodiment will then be described with reference to FIGS. 3 to 6. FIG. 3 is a flowchart for explaining the contents of the optical measurement control process performed by the specimen measurement system 30 according to the first embodiment. FIGS. 4 to 6 are diagrams for sequentially explaining the state of the specimen solution measured during the optical measurement control process, which is in the reaction space 50. In this embodiment, the optical measurement control process is performed by the control unit 20.

First, as shown in FIG. 3, the control unit 20 of the specimen measurement system 30 determines whether the measurement cartridge 100 is set to the specimen measurement device 32 (step S10). Specifically, the control unit 20 acquires the detection result from the cartridge sensor 24 with respect to the presence or the absence of reflected light to determine whether the measurement cartridge 100 is set to the specimen measurement device 32. If the reflected light is newly detected, the control unit 20 determines that the measurement cartridge 100 is newly set. If no reflected light is detected or the reflected light is continuously detected, the control unit 20 determines that no measurement cartridge 100 is newly set.

If the control unit 20 determines that no measurement cartridge 100 is newly set to the specimen measurement device 32 (NO in step S10), step S10 is repeated until a measurement cartridge 100 is newly set.

If the control unit 20 determines that a measurement cartridge 100 is newly set to the specimen measurement device 32 (YES in step S10), the control unit 20 activates the first magnetic field application unit 10a of the magnetic field application unit 10 to generate an upward magnetic field (step S12). While the upward magnetic field is being generated, the user introduces the specimen solution into the reaction space 50 of the measurement cartridge 100 through the inlet 51.

FIG. 4 is a cross-sectional view of the measurement cartridge 100 for explaining the state of the reaction space 50 when the specimen solution has been introduced into the reaction space 50. As shown in FIG. 4, if the specimen solution is introduced into the reaction space 50, the sealing film 40 formed of a water-soluble material is rapidly dissolves and the magnetic particles 9 sealed by the sealing film 40 disperse into the specimen solution. Since the upward magnetic field is generated, the magnetic particles 9 do not precipitate but move upward. Since the sealing film 40 dissolves, the first substance 6 fixed to the sensing area 101 is also exposed to the specimen solution.

The period of time during which the upward magnetic field is generated in step S12 may be arbitrarily set as long as it is sufficient to diffuse and move the magnetic particles 9 upward after the specimen solution is introduced into the reaction space 50. For example, the upward magnetic field may be generated for a period of time such as 10 seconds or 20 seconds after the control unit 20 detects that the measurement cartridge 100 is set in step S10. Alternatively, after the specimen solution is introduced into the reaction space 50, the specimen measurement system 30 may prompt the user to input information by means of a switch etc. and then the upward magnetic field may be generated for a period of time such as 5 seconds or 10 seconds based on the inputted information.

On the hand, when the specimen solution is introduced into the reaction space 50 of the measurement cartridge 100, the refractive index of the light in the sensing area 101 changes. Therefore, the detection unit 8 may detect the change in the refractive index in order to detect the introduction of the specimen solution. For example, the upward magnetic field may be generated for a predetermined period of time after the detection unit 8 detects the change in the refractive index of the light.

In the specimen measurement system 30 according to the first embodiment, the calculation unit 22 obtains the measurement result from the detection unit 8 while the upward magnetic field is being applied in step S12 or immediately after the application of the upward magnetic field in step S12 is finished. Thus, the calculation unit 22 obtains the intensity of light detected by the detection unit 8 and calculates an initial value of the intensity of the light.

Thereafter, as shown in FIG. 3, the control unit 20 stops activating the first magnetic field application unit 10a of the magnetic field application unit 10, and activates the second magnetic field application unit 10b, thereby generating a downward magnetic field (step S14). As a result, the magnetic particles 9 in the specimen solution precipitate while diffusing. It is highly possible that during the precipitation, the magnetic particles 9 react with the measurement object material 14 in the specimen solution. When the magnetic particles 9 reacted with the measurement object material 14 precipitate to the sensing area 101, the magnetic particles 9 are bonded with the first substance 6 fixed on the surface of the optical waveguide 3 in the sensing area 101 via the measurement object material 14. Since the reaction rate of the measurement object material 14 and the first substance 6 may not be sufficient if the magnetic field is applied, the generation of the downward magnetic field may be stopped for a certain period of time after step S14.

FIG. 5 is a cross-sectional view of the measurement cartridge 100 for explaining the state of the reaction space 50 in which the magnetic particles 9 precipitate. As shown in FIG. 5, the magnetic particles 9 reacted with the measurement object material 14 in the specimen solution are bonded with the first substance 6 via the measurement object material 14. The magnetic particles 9 that are not reacted with the measurement object material 14 are not bonded with the first substance 6.

The period of time during which the downward magnetic field is generated in step S14 may be arbitrarily set as long as it is sufficient for the magnetic particles 9 having moved upward to precipitate while diffusing. For example, the downward magnetic field may be generated for a predetermined period of time such as 10 seconds or 20 seconds after the generation of the upward magnetic field is stopped and the generation of the downward magnetic field is started.

Subsequently, the control unit 20 stops the activation of the second magnetic field application unit 10b of the magnetic field application unit 10 and activates the first magnetic field application unit 10a to generate the upward magnetic field as shown in FIG. 3 (step S16). As a result, the magnetic particles 9 that are not bonded with the first substance 6 fixed to the surface of the optical waveguide 3 move upward due to the upward magnetic field. On the other hand, the magnetic particles 9 that are bonded with the first substance 6 fixed to the surface of the optical waveguide 3 do not move upward. Therefore, the magnetic particles 9 bonded with the first substance 6 via the measurement object material 14 are left in the sensing area 101 on the surface of the optical waveguide 3.

FIG. 6 is a cross-sectional view of the measurement cartridge 100 for explaining the state of the reaction space 50 in which the magnetic particles 9 that are not bonded with the first substance 6 fixed to the surface of the optical waveguide 3 have moved upward in the specimen solution. As shown in FIG. 6, the magnetic particles 9 that are bonded with the first substance 6 via the measurement object material 14 are left in the sensing area 101 on the surface of the optical waveguide 3, but the magnetic particles 9 that are not reacted with the measurement object material 14 and not bonded with the first substance 6 are not left in the sensing area 101 on the surface of the optical waveguide 3.

After a predetermined period of time has passed since the application of the upward magnetic field starts in step S16, the calculation unit 22 obtains the measurement result from the detection unit 8. Specifically, the calculation unit 22 obtains the intensity of light detected by the detection unit 8 and calculates a detection result value. In this embodiment, the amount of the measurement object material 14 in the specimen solution may be measured by calculating the attenuation of the light intensity due to the magnetic particles 9 bonded with the first substance 6 via the measurement object material 14. The intensity of light propagating through the optical waveguide 3 changes depending on the amount of the magnetic particles 9 bonded with the first substance 6 fixed to the sensing area 101. Therefore, the absorbance of the light propagating through the optical waveguide 3 changes depending on the amount of the magnetic particles 9 bonded with the first substance 6 fixed in the sensing area 101. The calculation unit 22 uses this characteristic, and calculates a difference between the initial value of the light intensity measured in step S12 and the detection result value of the light intensity measured in step S16, and calculates the amount of the measurement object material 14 based on the difference therebetween, which is used as a signal reduction ratio.

In the first embodiment, the magnetic field application unit 10 corresponds to a magnetic field applicator, the substrate 1 and the optical waveguide 3 forms a substrate having a light-transmitting property, the detection unit 8 corresponds to a detector, the control unit 20 corresponds to a controller, and the calculation unit 22 corresponds to a calculator.

As described above, in the specimen measurement system 30 according to the first embodiment, since the specimen solution is introduced into the reaction space 50 of the measurement cartridge 100 while the upward magnetic field is being applied, the magnetic particles 9 may disperse into the specimen solution rapidly after the sealing film 40 formed of a water-soluble material dissolves. The magnetic particles 9 may be moved upward in the specimen solution due to the upward magnetic field.

Thereafter, the downward magnetic field is applied and the magnetic particles 9 precipitate in the specimen solution. During the precipitation, it is highly possible that the magnetic particles 9 may react with the measurement object material 14. Therefore, the accuracy of the measurement of the measurement object material 14 may be improved.

Furthermore, according to the present embodiment, the magnetic particles 9 are placed in the sensing area 101 on the surface of the optical waveguide 3 by the sealing film 40 formed of a water-soluble material. Therefore, in the manufacturing process of fixing the first substance 6 to the surface of the sensing area 101, the magnetic particles 9 may also be placed in the sensing area 101. As a result, it is not necessary to place the magnetic particles 9 in the measurement cartridge 100 in a separate manufacturing process, which reduces the costs for producing the measurement cartridge 100.

Incidentally, in the embodiment mentioned above, when it is detected that the measurement cartridge 100 is set to the specimen measurement device 32 in step 10 in FIG. 3, the first magnetic field application unit 10a of the magnetic field application unit 10 starts generating the upward magnetic field in step 12. However, a trigger to start generating the upward magnetic field is optional. For example, the user who tries to introduce the specimen solution into the reaction space 50 may input information via an operation switch, and the generation of the upward magnetic field may be started in step 12 in response to the trigger of the inputted information. That is, various kinds of triggers, which initiate the generation of the upward magnetic field by the first magnetic field application unit 10a of the magnetic field application unit 10, can be considered.

Second Embodiment

In the specimen measurement system 30 according to the first embodiment described above, the magnetic field application unit 10 includes the first magnetic field application unit 10a that generates the upward magnetic field and the second magnetic field application unit 10b that generates the downward magnetic field. On the other hand, a specimen measurement system 30 according to a second embodiment does not have the second magnetic field application unit 10b that generates the downward magnetic field, and the magnetic field application unit 10 includes the first magnetic field application unit 10a. The part of the configuration of the specimen measurement system 30 according to the second embodiment that is different from the configuration of the first embodiment will be described below.

Figure 7:
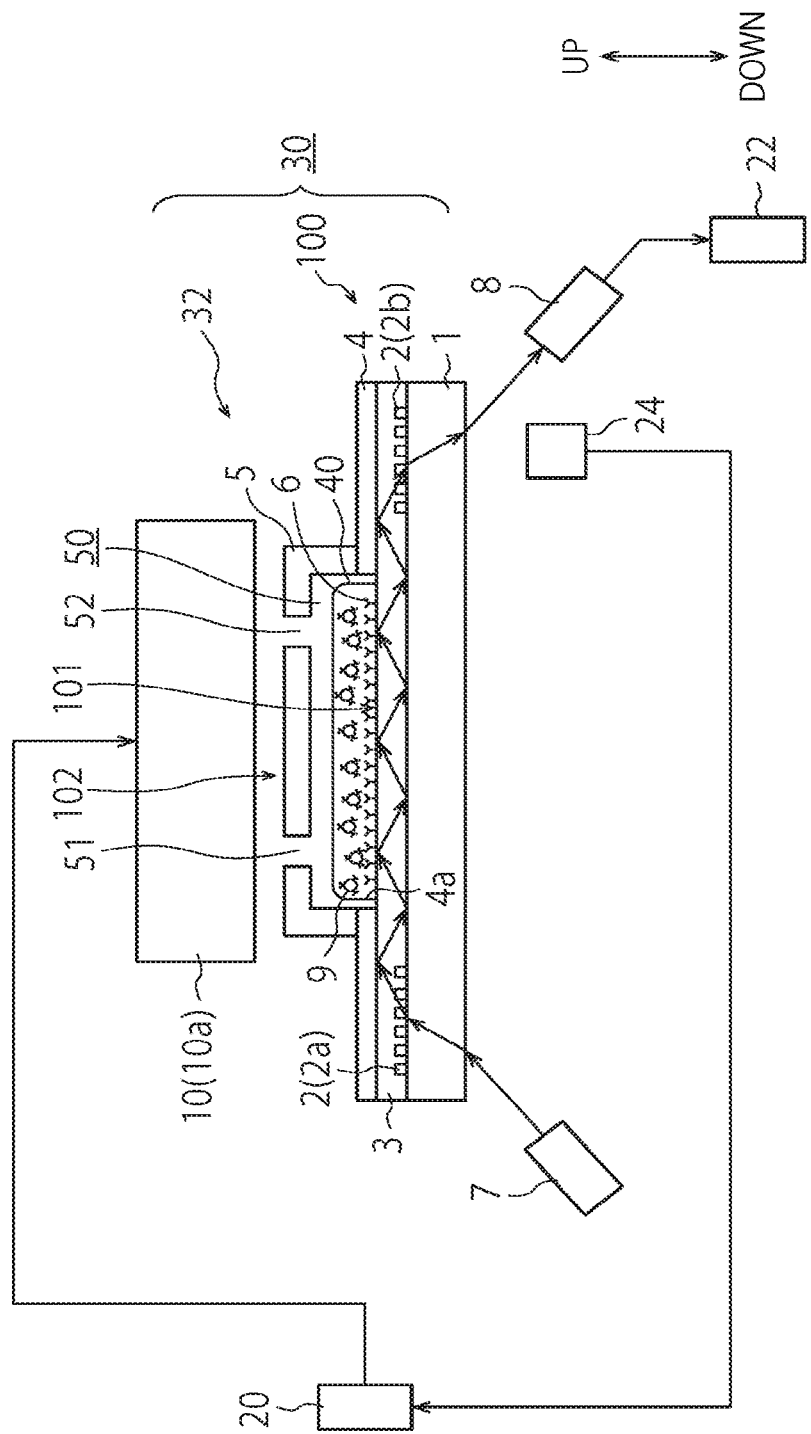
FIG. 7 is a block diagram illustrating an example of the entire configuration of a specimen measurement system according to a second embodiment.

FIG. 7 is a diagram for explaining an example of the entire configuration of the specimen measurement system 30 according to the second embodiment, and it corresponds to FIG. 1 showing the first embodiment described above. As shown in FIG. 7, the magnetic field application unit 10 according to this embodiment does not include the second magnetic field application unit 10b that generates the downward magnetic field, but includes the first magnetic field application unit 10a that generates the upward magnetic field.

Therefore, the control unit 20 does not include the switch 20a, and it is directly connected to the first magnetic field application unit 10a without using the switch 20a. The control unit 20 controls whether or not the first magnetic field application unit 10a is activated, and also the intensity of the magnetic field generated by the first magnetic field application unit 10a. The control unit 20 also controls the operation of the calculation unit 22, in the same manner as the control unit 20 according to the first embodiment described above.

Figure 8:
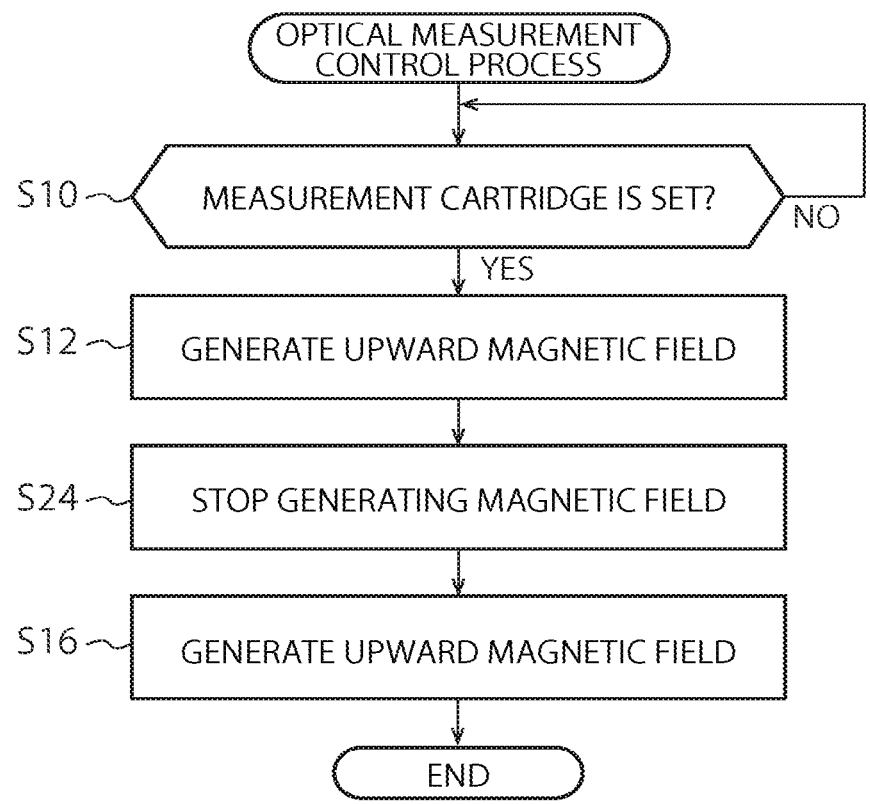
FIG. 8 is a flowchart for explaining the contents of an optical measurement control process performed by the specimen measurement system according to the second embodiment.

FIG. 8 is a flowchart for explaining the contents of an optical measurement control process performed by the specimen measurement system 30 according to the second embodiment. FIG. 8 corresponds to FIG. 3 showing the flowchart of the first embodiment. As shown in FIG. 8, step S10 and step S12 in the optical measurement control process according to the second embodiment are the same as those of the process according to the first embodiment described above. The second embodiment, however, differs from the first embodiment in step S24 that follows step S12.

Specifically, after the generation of the upward magnetic field in step S12, the control unit 20 of the specimen measurement system 30 according to the second embodiment stops the generation of the upward magnetic field (step S24). Since the second magnetic field application unit 10b is not provided to the second embodiment, the downward magnetic field cannot be generated. Therefore, the control unit 20 stops the activation of the first magnetic field application unit 10a. As a result, the magnetic particles 9 having moved to the upper portion of the specimen solution precipitate by their own weights due to the gravity while naturally diffusing in the specimen solution. It is highly possible that during the precipitation, the magnetic particles 9 react with the measurement object material 14.

The period of time in which the generation of the magnetic field is stopped may be arbitrarily determined, but it would be longer than the period of time in which the downward magnetic field is generated in step S14 of the first embodiment. The reason for this is that, since the magnetic particles 9 precipitate by their own weights while acting with the measurement object material 14, it takes a longer time for the magnetic particles 9 to reach the sensing area 101 on the surface of the optical waveguide 3. For example, the generation of the magnetic field may be stopped for a predetermined period of time such as 20 seconds or 30 seconds after the generation of the upward magnetic field is stopped.

Thereafter, the first magnetic field application unit 10a is activated in step S16, in the same manner as the first embodiment described above, thereby generating the upward magnetic field (step S16). As a result, the magnetic particles 9 that are not bonded with the first substance 6 fixed on the surface of the optical waveguide 3 move upward in accordance with the upward magnetic field. The timing at which the calculation unit 22 measures the intensity of light as an initial value, and measures the intensity of light to obtain a detection result value is the same as those in the first embodiment.

As described above, in the specimen measurement system 30 according to the second embodiment, the specimen solution is introduced into the reaction space 50 of the measurement cartridge 100 while the upward magnetic field is being applied. Therefore, after the water-soluble material dissolves into the specimen solution, the magnetic particle 9 may rapidly disperse into the specimen solution. That is, since the upward magnetic field is applied to the measurement cartridge 100, the magnetic particles 9 may move upward in the specimen solution.

Thereafter, the generation of the magnetic field is stopped, and the magnetic particles 9 precipitate by their own weights in the specimen solution due to the gravity. It is highly possible that the magnetic particles 9 react with the measurement object material 14 during the precipitation. Therefore, the accuracy of the measurement of the measurement object material 14 may be improved.

Furthermore, since the magnetic field application unit 10 does not include the second magnetic field application unit 10b that generates the downward magnetic field, the costs for producing the magnetic field application unit 10 may be reduced, which leads to the reduction in the costs of producing the specimen measurement device 32 and the specimen measurement system 30.

While certain embodiments have been described, these embodiments have been presented by way of example only, and are not intended to limit the scope of the inventions. The novel devices and methods described above may be embodied in a variety of other forms. Furthermore, various omissions, substitutions and changes may be made on the devices and methods described above without departing from the spirit of the inventions. The accompanying claims and their equivalents are intended to cover such embodiments and their modifications as would fall within the scope and spirit of the inventions.

The invention claimed is:
1. A specimen measurement device which detects a measurement object material, comprising:
a magnetic field generator configured to apply a magnetic field to a measurement cartridge, wherein the measurement cartridge comprises a substrate having a light-transmitting property, at least one first substance fixed on the substrate and specifically reacting with the measurement object material, at least one magnetic particle, and at least one second substance fixed on the at least one magnetic particle and specifically acting with the measurement object material;
a detector configured to detect light passing through the substrate; and
a controller configured to control the magnetic field generator to perform, after the measurement cartridge is set, a first magnetic field applying operation to apply a first magnetic field in a direction to move the at least one magnetic particle away from the substrate while a specimen solution containing the measurement object material is being introduced into the measurement cartridge, and then perform a second magnetic field applying operation to apply a second magnetic field in a direction to move the at least one magnetic particle toward the substrate, so that the at least one first substance and the at least one second substance are able to be bonded with each other via the measurement object material, wherein the controller starts:

the second magnetic field applying operation after the first magnetic field applying operation is stopped; and a third magnetic field applying operation to apply a third magnetic field in a direction to move the magnetic particle away from the substrate after the second field applying operation is stopped.

2. The specimen measurement device according to claim 1, further comprising a calculator configured to obtain a first measurement result using a detection result of the detector during the first magnetic field applying operation or immediately after the first magnetic field applying operation.

3. The specimen measurement device according to claim 1, wherein the magnetic field generator includes:

a first magnetic field generator configured to generate the first magnetic field in the first magnetic field applying operation, wherein the first magnetic field generator is located in a first direction with respect to the substrate, the first direction being a direction to move the at least one magnetic particles away from the substrate; and a second magnetic field generator configured to generate the second magnetic field in the second magnetic field applying operation, wherein the second magnetic field generator is located in a second direction with respect to the substrate, the second direction being a direction to move the at least one magnetic particles toward the substrate.

4. The specimen measurement device according to claim 1, wherein, in the measurement cartridge, the at least one magnetic particle is sealed by a water-soluble material and kept on a surface of the substrate.

5. The specimen measurement device according to claim 1, further comprising a cartridge sensor configured to detect that the measurement cartridge is set to the specimen measurement device.

6. The specimen measurement device according to claim 5, wherein the controller starts the first magnetic field applying operation when the cartridge sensor detects that the measurement cartridge is set.

7. The specimen measurement device according to claim 6, wherein the controller starts the second magnetic field applying operation when a first predetermined period of time has passed since the controller starts the first magnetic field applying operation.

8. The specimen measurement device according to claim 7, wherein the controller starts the third magnetic field applying operation to apply the third magnetic field in a direction to move the magnetic particle away from the substrate when a second predetermined period of time has passed since the second magnetic field applying operation is started.

9. The specimen measurement device according to claim 8, wherein the controller obtains a second measurement result when a third predetermined period of time has passed since the third magnetic field applying operation is started.

10. The specimen measurement device according to claim 1, wherein the controller starts the first magnetic field applying operation in response to information inputted by a user.

11. The specimen measurement device according to claim 1, further comprising a cartridge sensor configured to detect, using reflected light, that the measurement cartridge is set to the specimen measurement device.

12. The specimen measurement device according to claim 11, wherein the controller starts the first magnetic field applying operation when the cartridge sensor detects that the measurement cartridge is set.

13. The specimen measurement device according to claim 12, wherein the controller starts the second magnetic field applying operation when a first predetermined period of time has passed since the controller starts the first magnetic field applying operation.

* * * * *